United States Patent [19]  [11] 4,346,082
Revici  [45] Aug. 24, 1982

[54] METHOD OF EMPLOYING THERAPEUTIC COMPOSITION COMPRISING AMMONIUM OR SUBSTITUTED AMMONIUM COMPOUNDS FOR TREATMENT OF ALCOHOLISM

[75] Inventor: Emanuel Revici, New York, N.Y.

[73] Assignee: The Vinoxen Company, New York, N.Y.

[21] Appl. No.: 239,091

[22] Filed: Feb. 27, 1981

Related U.S. Application Data

[63] Continuation of Ser. No. 109,699, Jan. 4, 1980, abandoned, which is a continuation of Ser. No. 2,591, Jan. 11, 1979, abandoned, which is a continuation of Ser. No. 839,567, Oct. 5, 1977, abandoned.

[51] Int. Cl.³ .................... A61K 33/04; A61K 33/02; A61K 31/19
[52] U.S. Cl. ................................. 424/162; 424/166; 424/317
[58] Field of Search ...................... 424/166, 162, 317

[56] References Cited
PUBLICATIONS

Matena Medica & Therapeutics, 6th Ed. (1907) pub. by the Ellingwoods Therapeutist Co. Chicago, pp. 236–239.
Hughes Practice of Medicine, 13th Ed. published by P. Blakeston's Son & Co. Phila. Pa. pp. 190–197.
The Dispensatory of the U.S.A. 24th Ed. (1947) published by J. B. Lippincott Co. Phila. Pa. pp. 72, 73, 1099, 1100, 1591.

*Primary Examiner*—Donald B. Moyer
*Attorney, Agent, or Firm*—Millen & White

[57] ABSTRACT

This invention relates to a method of treating alcoholism and for eliminating, reducing or preventing alcohol intoxication or the manifestations of alcohol intoxication in humans by administering thereto a therapeutic composition comprising an ammonium compound or compounds, said compounds and each of said compounds having a pH greater than 5.0 when in aqueous solution at a concentration of 5 grams per 100 grams of solution (5 weight percent), and particularly ammonium salt compounds containing ammonium cations and sulfur anions.

14 Claims, No Drawings

METHOD OF EMPLOYING THERAPEUTIC COMPOSITION COMPRISING AMMONIUM OR SUBSTITUTED AMMONIUM COMPOUNDS FOR TREATMENT OF ALCOHOLISM

This is a continuation of application Ser. No. 109,699, filed Jan. 4, 1980, now abandoned, which is a continuation of Ser. No. 002,591, filed Jan. 11, 1979, now abandoned, which in turn is a continuation of Ser. No. 839,567, filed Oct. 5, 1977, also abandoned.

BACKGROUND OF THE INVENTION

Various pharmaceutical uses of ammonium compounds have long been recognized. For example, the following ammonium compounds (as listed in Hackh's Chemical Dictionary, 4th Ed. McGraw-Hill, New York pages 37-40) have the following medicinal uses as indicated therein. Ammonium acetate is used as an antipyretic and diaphoretic antidote in formaldehyde poisoning; ammonium benzoate has been used as an antipyretic, diuretic and alternative; ammonium bromide is used to treat neuralgia; ammonium carbamate is used as a stimulant; ammonium carbonate carbamate (Hartshorn salt) is used as a heart stimulant; ammonium chloride is used as an expectorant, stimulant diuretic or disphoretic, as well as externally; ammonium formate is used as an antiseptic; ammonium hypophosphite is a nerve tonic; ammonium thiosulfate can be used as an antiseptic, ammonium iodide is used to treat syphilis and leprosy; ammonium persulfate is used as a disinfectant; ammonium phosphate can be used as an antirheumatic; ammonium salicylate is used as an antirheumatic, antipyretic, expectorant, and bactericide; and ammonium valerate is a hypnotic, sedative, and tonic. Ammonium thiosulfate has long been a standard industrial commodity, and U.S. Pat. No. 3,350,168 to Ziegler indicates that U.S. consumption of ammonium thiosulfate totaled 30,000 tons per year at the time of such patent. U.S. Pat. No. 3,890,428 to Jayawant and U.S. Pat. No. 3,973,793 to Netzger et al. indicates that ammonium thiosulfate has long been employed as a photographic fixer.

A publication entitled "Testing for a 'Sobering Pill'," DOT HS-801 208 (1974), available from National Technical Information Service, Springfield, Va. 22151, discloses that a number of compounds, including ammonium chloride, were investigated to determine their potential for blocking or neutralizing the effect of alcohol on a human brain. While the most effective amethystic agent (a preventive antidote of drunkenness) found was L-dopa, with respect to ammonium chloride, which has a relatively low molar pH in aqueous solution, the publication concludes that ammonium chloride does not appear to act as an amethystic agent.

None of the reference teaches the use of the compositions of the present invention as a treatment for alcoholism or eliminating and preventing alcohol intoxication or the manifestations of alcohol intoxication.

SUMMARY OF THE INVENTION

The invention relates to a method of treating alcoholism and for eliminating, reducing or preventing alcohol intoxication or the manifestations of alcohol intoxication in humans by administering thereto an ammonium compound or compounds, said compounds and each of said compounds having a pH greater than 5.0 moles when in aqueous solution at a concentration of 5 weight percent. Especially preferred embodiments are the salt compounds containing ammonium cations and sulfur anions. The ammonium compound can be administered to the patient by various known methods of injection or orally as by capsule form.

DETAILED DESCRIPTION OF THE INVENTION

It is to be especially noted that applicant is not claiming a cure for alcoholism; rather, this invention encompasses a method to treat acute and chronic effects of alcoholism or its manifestations or to prevent or reduce alcohol intoxication in which are used therapeutic compositions comprising any non-toxic compound having ammonium cations or substituted ammonium in its molecule, or mixtures or more than one such compound wherein said compound and each of said compounds have a pH greater than 5.0 when in aqueous solution at a concentration of 5 weight percent. Such preparations administered to humans may also help in detoxification of patients addicted to alcohol.

Concerning the aforesaid pH requirement, it is to be observed that, for example, within a series of ammonium salts of a polybasic acid the most preferred therapeutic agent is that molecule with no acidic hydrogen ion; the next most preferred is that molecule with one acidic hydrogen ion, and the least preferred is that with only one ammonium ion. For example, triammonium phosphate is preferred over diammonium monohydrogen phosphate, which in turn is preferred over monoammonium dihydrogen phosphate.

Also comprising a class of preferred embodiments are those agents containing sulfur in the anion portion of the molecule. Exemplary of effective agents containing sulfur are ammonium thiosulfate, ammonium sulfate, ammonium sulfamate and ammonium tetrathionate. The most effective of these is ammonium thiosulfate, with ammonium sulfate for treatment of the effects of alcohol in humans being somewhat less effective.

Ammonium acetate has likewise been shown to be a preferred embodiment of the instant invention.

Especially preferred are those ammonium salts of weaker acids and the most basic ammonium salts of polyprotic acids, that is, salts with comparatively basic aqueous solutions. To exemplify the preferred anions, namely those forming aqueous solutions with a pH greater than 5.0 at a concentration of 5 weight percent (5 grams of salt per 100 grams of solution), the following table gives measured pH values for certain salt species mentioned in this application.

TABLE I

| Salt | pH of 5 Weight Percent Solution |
| --- | --- |
| Ammonium thiosulfate | 5.966 |
| Ammonium sulfamate | 5.335 |
| Ammonium acetate | 6.790 |
| Ammonium sulfate | 5.263 |
| Ammonium chloride | 4.761 |

For each salt, 5.000 grams of reagent grade material was weighed and added to 95.00 grams of water. An Orion Ionalyzer Model digital 801 pH meter with glass electrode measured against a saturated calomel electrode was standardized by a pH 7.00 buffer. The instrument was allowed to equilibrate for three minutes between each sample, and the electrodes were rinsed with carbonate-free deionized water. Manual temperature control was set at 25° C. After the last sample was measured, the instrument was checked by measuring the pH 7.00 buffer solution and the first sample, and consistent readings were obtained.

Also contemplated within the scope of this invention are cations containing substituted ammonium, where one or more of the four hydrogen atmos attached to the nitrogen is substituted with, for example, an alkyl group such as methyl or ethyl. Such compounds are well recognized in the art, and the same preferred anions outlined above are preferred when combined to form salts of substituted ammonium cations. Only those anions which form nontoxic compounds with substituted ammonium cations are contemplated as within the scope of this invention.

It is contemplated that the dosage of the compound or compounds encompassed within the scope of this invention would be limited to that dosage normally toxic to a human subject, as determined by both body weight and the particular physiological constitution of the human subject. Furthermore, it is contemplated to limit the dosage of the compound or compounds of the invention to that dosage which, when given with alcohol, constitutes a non-toxic amount.

Notwithstanding the requirement that compositions falling within the scope of the instant invention be nontoxic, studies of acute subacute and chronic toxicity of ammonium thiosulfate, ammonium sulfate and ammonium acetate in mice and rats have shown a low toxicity for their administration through gastric catheter. Studies in humans have demonstrated likewise the nontoxicity of ammonium thiosulfate, ammonium sulfate and ammonium acetate to the extent that even repeated administration of up to 20 capsules per day (1 gram/capsule) for a period of 10 days produced no clinical or analytic noxious effects.

The compositions of the present invention can be prepared and suitably administered in any of a number of conventional ways, such as by incorporating the compound or compounds into gelatin capsules or any other conventional soluble capsule, in an amount up to about 1.2 grams of the compound or compounds per capsule; preferably the capsules should contain either about 0.5 grams or about 1.0 gram. The compound or compounds may also be administered in any conventional tablet form which may contain the same amount of the compound or compounds as the capsule. Likewise, the composition may be consumed orally in a non-capsule or non-tablet form, i.e., in a solution comprised of the compound or compounds of the invention, and, for example, a pharmaceutically acceptable carrier, or diluent, such as sterile water, wherein the solution may contain up to about 70% by weight of the compound or compounds of the invention. It may thus be administered in dropwise form until the desired equivalent amount of the compound or compounds is administered.

The compound or compounds of the invention may also be administered by injection, such as intramuscularly or intraperitoneally, wherein the solution to be injected comprises the compound or compounds of the invention and any conventional inert pharmaceutically acceptable carrier, or diluent, such as sterile water, and wherein the solution may contain up to about 10% by weight of the compound or compounds of the invention. The amount to be injected will depend on the equivalent amount of the compound or compounds that one desires to administer.

Although, as noted, the agents of the present invention can be injected in aqueous solution into the body, it is preferred that they be administered orally encapsulated in a conventional soluble capsule containing in solid form the prescribed dosage of preparation.

Concerning the specific amounts of the compound or compounds to be administered, this will be easily determinable by those skilled in the art and will depend, to a certain extent, upon the particular compound or compounds to be administered (for instance, it has been found that twice as much of ammonium sulfate and ammonium acetate as compared to ammonium thiosulfate is required to achieve the same result), whether one is treating those already subject to the effects of alcohol and exhibiting the manifestations of alcohol, or whether one is treating individuals so as to prevent the manifestations of alcohol from occurring in the first instance. It has been found to be an advantageous mode of preventing intoxication to administer to a patient one capsule containing approximately 1 gram of ammonium thiosulfate (twice the dosage for ammonium sulfate or ammonium acetate) approximately 40 minutes before consumption of the first intoxicating alcoholic drink and a second capsule after the third drink. In this manner, it was shown that approximately 5 to 7 alcoholic drinks may be consumed without any outward evidence of inebriation.

Another preferred mode for the application of the instant invention in the treatment of persons already partially subject to the effects of alcohol and exhibiting the manifestations of alcohol intoxication (i.e., after one or two alcoholic drinks) is to administer either one or two capsules, each containing approximately 1 gram of ammonium thiosulfate (or approximately 2 to 4 capsules, each containing 1 gram of ammonium sulfate or ammonium acetate).

For the treatment of those habitually addicted to alcohol, it has been found preferable to administer about 4 to 6 grams/day, i.e., 4 to 6 capsules, each containing 1 gram of ammonium thiosulfate (or approximately twice the dosage as in the case of ammonium sulfate or ammonium acetate) for two days and thereafter to reduce the dosage to approximately 1 to 2 grams/day as required.

A possible explanation for the activity of the ammonium salts of this invention is that such compositions counteract the effects in the body of fatty acids, and prevents conjugation of substances with positive polar groups. Any suggested mode of operation or explanation of the mechanism of activity of the present invention is not intended to limit the scope of the present invention, and an understanding of such mode or mechanism is not necessary for the successful practice of the present invention.

Tests of some of the compounds encompassed within the scope of this invention were carried out with mice to determine efficacy in altering the effects of alcohol administered to the test animals. Good results on the mice were also obtained with the use of ammonium acetate. A series of tests comparing the effects on mice of ammonium thiosulfate and ammonium sulfate indicate that both are approximately equally effective. It is expected, however, that the effect of ammonium thiosulfate in altering the effects of alcohol ingestion in humans is substantially greater than the effects of ammonium sulfate. Tests of some of the compounds encompassed within the scope of this invention were carried out with humans, and likewise, good results were obtained which demonstrate the efficacy of the instant invention.

Throughout the specification and claims reference to an alcoholic drink means reference to an aqueous mixture of ethanol containing about 15-25 grams of ethanol per drink.

EXAMPLE 1

Procedure—The following procedure was carried out for determining the $ED_{50}$ (effective dose which produces the desired effect in 50% of the test animals) of 30% (v/v) ethanol for neurological deficiency in fasted mice which had been previously pretreated with an aqueous solution of ammonium thiosulfate. Food, but not water, was removed from the cages of 50 adult male albino mice (Charles River) on the day of the test. Five hours later the fasted animals were pretreated orally with 0.6 ml/mouse of a 10% aqueous solution of ammonium thiosulfate. Thirty minutes later a freshly prepared solution of 30% (v/v) ethanol was administered orally to the animals in groups of 10, at doses ranging from 0.5 to 1.0 ml per mouse. Ten minutes after administering the ethanol the mice were placed individually on a rod rotating at 6 rpm. Neurological deficit was recorded if the animal was unable to remain on the rod for at least 10 seconds. A group of 10 fasted but non-pretreated mice all exhibited neurological deficit following a dose of 0.5 ml, thereby serving as controls on the activity of the freshly prepared ethanol solution.

Findings for individual animals (+)=neurological deficit, and (−)=no neurological deficit are shown below in Table II with the summary of results set forth in Table III. The oral $ED_{50}$ of ethanol in the ammonium thiosulfate solution pretreated animals is shown to be 0.76 ml, with 95% fiducial limits of 0.65 to 0.90 ml (determined graphically by a Litchfield and Wilcoxon plot).

The identical procedure was carried out for determining the oral $ED_{50}$ of 30% (v/v) ethanol for neurological deficit for non-pretreated mice: Freshly prepared 30% (v/v) ethanol was administered orally to adult male albino mice (fasted for 5 hours), in groups of 5 to 10, at doses ranging from 0.05 to 0.50 ml per mouse. Ten minutes later the animals were placed, individually, on a rotored, rotating at 6 rpm. Neurological deficit was again recorded (+) if the animal fell from the rod—i.e., did not possess the motor coordination required to 'logroll'—in less than 10 seconds. Absence of neurological deficit was similarly recorded (+) if the animal had sufficient coordination and muscular power to remain on the rotating rod for 10 seconds or more. The results are depicted in Table IV and summarized in Table V wherefrom it is seen that the dose of ethanol required to induce neurological deficit in 50% of the untreated animals (i.e., in this test the mice were in no way pretreated by the composition of the instant invention) is 0.17 ml/mouse, and the 95% fiducial limits (Litchfield and Wilcoxon graphic method used) was 0.13 to 0.22 ml/mouse.

Further, and in order to avoid physio-chemical problems that might, albeit remotely, arise if ethanol is administered orally, applicant also determined the intraperitoneal $ED_{50}$ of ethanol in fasted mice. The procedural details are identical to those followed in the case of the oral $ED_{50}$ except that the ethanol (30% v/v) was injected intraperitoneally. These results reveal that the intraperitoneal $ED_{50}$ of 30% ethanol is 0.15 ml/mouse (0.12-0.19 at 95% confidence limit) which is effectively the same as that obtained when ethanol was given orally. This latter finding confirms what has long been known, that ethanol is rapidly and fairly completely absorbed in the fasting state.

By so determining the $ED_{50}$ in non-pretreated mice, one could obtain statistically meaningful relative results in respect to the efficacy for the pretreatment of mice with ammonium thiosulfate.

Results—The $ED_{50}$ of 30% ethanol in non-pretreated mice was 0.17 ml/mouse; the comparable value for pretreated mice shown in the tables below is 0.76 ml/mouse. This establishes that following pretreatment with ammonium thiosulfate nearly five times as much ethanol was required to induce neurological deficit.

TABLE II

| Mouse No. | Weight (gm) | Dose of Ethanol (ml) | Dose of Ammonium Thiosulfate Solution (ml) | Results (+) = Fall 10 sec. (−) = No fall in 10 sec. |
|---|---|---|---|---|
| 1 | 33 | 0.5 | 0 - Control | + |
| 2 | 33 | " | " | + |
| 3 | 30 | " | " | + |
| 4 | 34 | " | " | + |
| 5 | 33 | " | " | + |
| 6 | 32 | " | " | + |
| 7 | 33 | " | " | + |
| 8 | 35 | " | " | + |
| 9 | 36 | " | " | + |
| 10 | 39 | " | " | + |
| 11 | 26 | " | 0.6 | − |
| 12 | 24 | " | " | − |
| 13 | 22 | " | " | − |
| 14 | 26 | " | " | − |
| 15 | 29 | " | " | − |
| 16 | 25 | " | " | − |
| 17 | 25 | " | " | − |
| 18 | 25 | " | " | − |
| 19 | 25 | " | " | + |
| 20 | 30 | " | " | − |
| 21 | 23 | 0.75 | 0.6 | + |
| 22 | 26 | " | " | ° |
| 23 | 29 | " | " | − |
| 24 | 26 | " | " | − |
| 25 | 24 | " | " | + |
| 26 | 26 | " | " | − |
| 27 | 24 | " | " | + |
| 28 | 29 | " | " | − |
| 29 | 30 | " | " | − |
| 30 | 28 | " | " | − |
| 31 | 31 | 1.00 | 0.0 | + |
| 32 | 29 | " | " | + |
| 33 | 27 | " | " | + |
| 34 | 30 | " | " | + |
| 35 | 26 | " | " | + |
| 36 | 30 | " | " | + |
| 37 | 28 | " | " | + |
| 38 | 29 | " | " | + |
| 39 | 23 | " | " | + |
| 40 | 29 | " | " | + |
| 41 | 26 | 0.63 | 0.6 | − |
| 42 | 28 | " | " | + |
| 43 | 29 | " | " | − |
| 44 | 26 | " | " | − |
| 45 | 29 | " | " | − |
| 45 | 29 | " | " | − |
| 46 | 28 | " | " | − |
| 47 | 27 | " | " | − |
| 48 | 27 | " | " | + |
| 49 | 29 | " | " | − |
| 50 | 29 | " | " | − |
| 51 | 27 | 0.87 | 0.6 | + |
| 52 | 23 | " | " | + |
| 53 | 27 | " | " | − |
| 54 | 25 | " | " | + |
| 55 | 26 | " | " | + |
| 56 | 24 | " | " | + |
| 57 | 27 | " | " | − |
| 58 | 25 | " | " | + |

TABLE II-continued

| Mouse No. | Weight (gm) | Dose of Ethanol (ml) | Dose of Ammonium Thiosulfate Solution (ml) | Results (+) = Fall 10 sec. (−) = No fall in 10 sec. |
|---|---|---|---|---|
| 59 | 27 | " | " | − |
| 60 | 27 | " | " | + |

TABLE III

| | Summary | | |
|---|---|---|---|
| Ethanol (ml Per Mouse) | Fraction Falling From Rod in 10 sec. | Percent Falling | $ED_{50}$ (ml) (95% Limit) |
| 0.50 | 1/10 | 10 | |
| 0.63 | 2/10 | 20 | |
| 0.75 | 4/10 | 40 | |
| 0.87 | 7/10 | 70 | 0.76 (0.65–0.90) |
| 1.00 | 10/10 | 100 | |

TABLE IV

| Mouse No. | Weight (gm) | Dose of Ethanol (ml) | Results (+) = Fall 10 sec. (−) = No fall in 10 sec. |
|---|---|---|---|
| 1 | 22 | 0.5 | + |
| 2 | 22 | " | + |
| 3 | 23 | " | + |
| 4 | 22 | " | + |
| 5 | 22 | " | + |
| 6 | 22 | 0.1 | − |
| 7 | 24 | " | − |
| 8 | 21 | " | − |
| 9 | 22 | " | − |
| 10 | 22 | " | − |
| 11 | 22 | 0.5 | + |
| 12 | 22 | — | + |
| 13 | 24 | " | + |
| 14 | 23 | " | + |
| 15 | 18 | " | + |
| 16 | 22 | 0.2 | + |
| 17 | 21 | " | + |
| 18 | 23 | " | − |
| 19 | 23 | " | − |
| 20 | 21 | " | + |
| 21 | 21 | " | + |
| 22 | 24 | " | − |
| 23 | 24 | " | + |
| 24 | 22 | " | + |
| 25 | 22 | " | + |
| 26 | 20 | 0.1 | − |
| 27 | 23 | " | − |
| 28 | 25 | " | − |
| 29 | 22 | " | + |
| 30 | 21 | " | + |
| 31 | 21 | 0.15 | − |
| 32 | 21 | " | − |
| 33 | 20 | 0.15 | − |
| 34 | 21 | " | − |
| 35 | 22 | " | − |
| 36 | 24 | " | + |
| 37 | 20 | " | + |
| 38 | 22 | " | + |
| 39 | 22 | " | + |
| 40 | 19 | " | + |
| 41 | 20 | 0.05 | − |
| 42 | 20 | " | − |
| 43 | 19 | " | − |
| 44 | 23 | " | − |
| 45 | 24 | " | − |
| 46 | 19 | 0.30 | − |
| 47 | 21 | " | + |
| 48 | 22 | " | + |
| 49 | 21 | " | + |
| 50 | 21 | " | + |

TABLE V

| | Summary | | |
|---|---|---|---|
| Ethanol Dose (ml Per Mouse) | Fraction Falling From Rod in 10 sec. | Percent Falling | $ED_{50}$ (ml) (95% Limit) |
| 0.05 | 0/5 | 0 | |
| 0.10 | 2/10 | 20 | |
| 0.15 | 4/10 | 40 | |
| 0.20 | 7/10 | 70 | 0.17 (0.13–0.22) |
| 0.30 | 4/5 | 80 | |
| 0.50 | 10/10 | 100 | |

EXAMPLE 2

This Example compares the effectiveness of ammonium thiosulfate and ammonium sulfate as inhibitors of ethanol-induced neurological deficit in fasted mice. Each composition was prepared freshly as a 10% aqueous solution from the crystalline preparation. A dose of 0.6 ml/mouse was administered orally to 10 mice for each compound. Thirty minutes later 0.5 ml/mouse of 30% (v/v) ethanol was given orally to each mouse and, 10 minutes later, the animals were tested for the presence or absence of neurological deficit in the usual manner as described in Example 1. A group of 10 untreated mice were used as controls. The results are shown in Table VI with the summary of the results in Table VII.

Results—It is clear that both ammonium thiosulfate and ammonium sulfate were highly effective as inhibitors of ethanol-induced neurological deficit at the dose used. It is equally clear that the two compounds were essentially equipotent on the basis of this single test.

TABLE VI

| Mouse No. | Weight (gm) | Dose of Ammonium Thiosulfate (ml) | Dose of 30% Ethanol (ml) | Results (+ = Fall in 10 sec. (−) = No Fall in 10 sec. |
|---|---|---|---|---|
| 1 | 29 | 0.6 | 0.5 | − |
| 2 | 29 | " | " | − |
| 3 | 28 | " | " | − |
| 4 | 27 | " | " | + |
| 5 | 28 | " | " | − |
| 6 | 25 | " | " | " |
| 7 | 27 | " | " | − |
| 8 | 26 | " | " | − |
| 9 | 26 | " | " | − |
| 10 | 26 | " | " | + |

| Mouse No. | Weight (gm) | Dose of Ammonium sulfate (ml) | Dose of 30% Ethanol (ml) | Results |
|---|---|---|---|---|
| 11 | 27 | 0.6 | " | − |
| 12 | 28 | " | " | + |
| 13 | 29 | " | " | + |
| 14 | 27 | " | " | − |
| 15 | 30 | " | " | − |
| 16 | 25 | " | " | − |
| 17 | 30 | " | " | + |
| 18 | 28 | " | " | − |
| 19 | 30 | " | " | − |
| 20 | 26 | " | " | − |
| 21 | 30 | Control - no pretreatment | " | + |
| 22 | 28 | " | " | + |
| 23 | 24 | " | " | + |
| 24 | 25 | " | " | + |
| 25 | 26 | " | " | + |
| 26 | 27 | " | " | + |

TABLE VI-continued

| Mouse No. | Weight (gm) | Dose of 30% Ethanol (ml) | Results (+ = Fall in 10 sec. (−) = No Fall in 10 sec. |
|---|---|---|---|
| 27 | 25 | " | + |
| 28 | 25 | " | + |
| 29 | 28 | " | + |
| 30 | 26 | " | + |

TABLE VII

Summary

| Compound | Dose ml/mouse | Ethanol | Route | No. Protected/ No. Treated |
|---|---|---|---|---|
| Ammonium thiosulfate + 30% Ethanol | 0.6 | 0.5 | Oral | 8/10 |
| Ammonium sulfate + 30% Ethanol | 0.6 | 0.5 | Oral | 7/10 |
|  | 0 | 0.5 | Oral | 0/10 |

EXAMPLE 3

This Example sets forth the oral $Ed_{50}$ of ammonium thiosulfate vs. ethanol-induced neurological deficit in fasted mice. The mice used in this study appeared to be in good health. They were deprived of food, but not water, for a period of five hours preceding the test. A 10% aqueous solution of ammonium thiosulfate was prepared from the crystalline material and appropriate amounts of distilled water were added to provide solutions containing 7.5, 5.0, 2.5, and 1.25% ammonium thiosulfate. A dose of 0.6 ml/mouse of all five ammonium thiosulfate solutions was administered orally. Ten minutes later the animals were tested for neurological deficit or its absence in the usual manner as described in Example 1. A separate group of fasted by non-pretreated mice served as ethanol controls. The results are set forth in Table VIII and summarized in Table IX.

Results—It is shown that, using 0.6 ml/mouse as the basic dose, the percent of pure ammonium thiosulfate required to protect 50% of the mice against ethanol-induced neurological deficit was 3.6 (2.63–4.93%).

TABLE VIII

| Mouse No. | Weight (nm) | Percent Ammonium Thiosulfate (0.6 ml/mouse) | Dose 30% Ethanol (ml/mouse) | Results (+) = Fall in 10 sec. (−) = No Fall in 10 sec. |
|---|---|---|---|---|
| 1 | 32 | 10.0 | 0.5 | + |
| 2 | 32 | " | " | − |
| 3 | 27 | " | " | − |
| 4 | 29 | " | " | − |
| 5 | 31 | " | " | − |
| 6 | 34 | " | " | − |
| 7 | 34 | " | " | + |
| 8 | 32 | " | " | − |
| 9 | 35 | " | " | − |
| 10 | 35 | " | " | − |
| 11 | 34 | 7.5 | " | − |
| 12 | 28 | " | " | − |
| 13 | 35 | " | " | − |
| 14 | 32 | " | " | − |
| 15 | 31 | " | " | − |
| 16 | 33 | 41 | " | + |
| 17 | 33 | " | " | − |
| 18 | 30 | " | " | − |
| 19 | 35 | " | " | + |
| 20 | 32 | " | " | − |
| 21 | 30 | 5.0 | " | + |
| 22 | 31 | " | " | + |
| 23 | 30 | " | " | − |
| 24 | 28 | " | " | − |
| 25 | 33 | " | " | − |
| 26 | 32 | " | " | − |
| 27 | 34 | " | " | + |
| 28 | 32 | " | " | − |
| 29 | 31 | " | " | − |
| 30 | 30 | " | " | − |
| 31 | 31 | 2.5 | " | + |
| 32 | 30 | " | " | − |
| 33 |  | " | " | + |
| 34 | 31 | " | " | + |
| 35 | 34 | " | " | + |
| 36 | 34 | " | " | + |
| 37 | 28 | " | " | − |
| 38 | 29 | " | " | + |
| 38 | 29 | " | " | + |
| 39 | 30 | " | " | + |
| 40 | 30 | " | " | + |
| 41 | 30 | 1.25 | " | + |
| 42 | 34 | " | " | + |
| 43 | 29 | " | " | + |
| 44 | 33 | " | " | + |
| 45 | 36 | " | " | + |
| 46 | 33 | " | " | + |
| 47 | 32 | " | " | + |
| 48 | 31 | " | " | + |
| 49 | 30 | " | " | + |
| 50 | 32 | " | " | + |
| 51 | 32 | 0 - Control | " | + |
| 52 | 33 | " | " | + |
| 53 | 33 | " | " | + |
| 54 | 33 | " | " | + |
| 55 | 36 | " | " | + |
| 56 | 35 | " | " | + |
| 57 | 30 | " | " | + |
| 58 | 32 | " | " | + |
| 59 | 33 | " | " | + |
| 60 | 31 | " | " | + |

TABLE IX

Summary

| Dose of Ammonium Thiosulfate (%) | Dose of Ammonium Thiosulfate (ml/mouse) | Fraction Protected | Percent | $ED_{50}$ (%) | 95% Confidence Limits |
|---|---|---|---|---|---|
| 0 - Controls | — | 0.10 | 0 | | |
| 1.25 | 0.6 | 0/10 | 0 | | |
| 2.5 | " | 3/10 | 30 | | |
| 5.0 | " | 7/10 | 70 | 3.6 | 2.63–4.93 |
| 7.5 | " | 8/10 | 80 | | |
| 10.0 | " | 8/10 | 80 | | |

EXAMPLE 4

More than one hundred individuals who had consumed 1 or 2 alcoholic drinks, and who had thus demonstrated certain and typical early manifestations of the effects of the alcohol, were given 1 or 2 capsules, each containing 1 gram of ammonium thiosulfate. These individuals were thereafter able to consume additional alcoholic drinks, in some cases, up to 8 additional drinks without exhibiting any of the typical and usual manifestations of the effects of alcohol.

I claim:

1. A method for treating alcoholism or for eliminating, reducing or preventing alcohol intoxication or the manifestation of alcohol intoxication in a host, which comprises administering thereto a therapeutic composition comprising a non-toxic compound containing a cation selected from the group consisting of ammonium and substituted ammonium, and wherein the anion portion of the compound contains sulfur, said compound having a pH greater than about 5.0 when in aqueous solution at a concentration of 5 grams per 100 grams of solution, in an amount sufficient to eliminate, reduce or prevent alcohol intoxication or the manifestations of alcohol intoxication.

2. The method of claim 1 wherein the compound containing sulfur in its anion portion contains an anion selected from the group consisting of thiosulfate, sulfate and sulfamate.

3. The method of claim 2 wherein the compound is ammonium thiosulfate.

4. The method of claim 2 wherein the compound is ammonium sulfate.

5. The method of claim 1 wherein the therapeutic composition is administered orally in a soluble capsule form, said capsule containing up to about 1.2 grams of said compound.

6. The method of claim 5 wherein the capsule contains about 1 gram of said compound.

7. The method of claim 1 wherein the therapeutic composition is administered orally and comprises a pharmaceutically acceptable carrier, said composition for oral administration containing up to about 70% by weight of said compound.

8. The method of claim 1 which comprises administering to an individual prior to consumption of alcohol, in capsule form, about 1 gram of ammonium thiosulfate and thereafter, subsequent to consumption of alcohol, administering to said individual, in capsule form, about 1 gram of ammonium thiosulfate.

9. The method of claim 1 which comprises administering to an individual exhibiting the manifestations of alcohol intoxication, in capsule form, about 1 to 2 grams of ammonium thiosulfate.

10. The method of claim 1 which comprises administering to an individual habitually addicted to alcohol, in capsule form, about 4 to 6 grams/day of ammonium thiosulfate for a period of one day and thereafter administering to said individual about 1 to 2 grams/day of ammonium thiosulfate.

11. The method of claim 1 wherein the therapeutic composition is administered by injection and comprising a pharmaceutically acceptable carrier, said composition for injectable administration containing up to about 10% by weight of said compound.

12. The method of claim 1 which comprises administering to an individual prior to consumption of alcohol, in capsule form, about 2 grams of ammonium sulfate and thereafter, subsequent to consumption of alcohol, administering to said individual, in capsule form, about 2 grams of ammonium sulfate.

13. The method of claim 1 which comprises administering to an individual exhibiting the manifestations of alcohol intoxication, in capsule form, about 2 to 4 grams of ammonium sulfate.

14. The method of claim 1 which comprises administering to an individual habitually addicted to alcohol, in capsule form, about 8 to 12 grams/day of ammonium sulfate, for a period of one day and thereafter administering to said individual about 2 to 4 grams/day of ammonium sulfate.

* * * * *